United States Patent [19]

Maudsley

[11] Patent Number: 4,689,567
[45] Date of Patent: Aug. 25, 1987

[54] NMR FOURIER IMAGING FROM MULTIPLE ECHOES

[75] Inventor: Andrew Maudsley, New York, N.Y.

[73] Assignee: Advanced NMR Systems, Inc., Woburn, Mass.

[21] Appl. No.: 826,079

[22] Filed: Feb. 4, 1986

Related U.S. Application Data

[63] Continuation-in-part of Ser. No. 616,283, Jun. 1, 1984, abandoned.

[51] Int. Cl.$^4$ ............................................. G01R 33/20
[52] U.S. Cl. ................................... 324/309; 324/312
[58] Field of Search .............. 324/307, 309, 311, 312

[56] References Cited

U.S. PATENT DOCUMENTS

| | | | |
|---|---|---|---|
| 4,431,968 | 2/1984 | Edelstein et al. | 324/309 |
| 4,451,788 | 5/1984 | Edelstein et al. | 324/309 |
| 4,471,305 | 9/1984 | Crooks et al. | 324/309 |
| 4,532,474 | 6/1985 | Edelstein | 324/309 |
| 4,570,119 | 2/1986 | Wehrli et al. | 324/309 |
| 4,599,565 | 7/1986 | Hoenninger, III et al. | 324/309 |

Primary Examiner—Stewart J. Levy
Assistant Examiner—Kevin D. O'Shea
Attorney, Agent, or Firm—Ostrolenk, Faber, Gerb & Soffen

[57] ABSTRACT

Fourier images based on multiple NMR echoes may be obtained using the method and apparatus disclosed. A sequence of pulses and gradients are applied to the object to be imaged. The pulses begin with an excitation pulse, which is followed by a series of refocusing pulses. In order to compensate for phase error in the refocusing pulses, the refocusing pulses are applied along alternating X and Y axes in the rotating frame of reference. The echoes are then coherently added to reserve phase information. Alternate echoes may be time reversed and their complex conjugate may be taken to permit coherent addition. Alternatively, the even echoes may be added separately from the odd echoes to produce separate data sets. The pulse and gradient switching sequence provides sign reversals such that any baseline component will be cancelled by the coherent addition. Before or after coherent addition, the echoes are transformed, and after forming a combined data set from a series of echo sequences, the combined data set is again transformed to produce an image of the object.

12 Claims, 19 Drawing Figures

ODD ECHO

FIG. 5A.

EVEN ECHO

NMR FOURIER IMAGING FROM MULTIPLE ECHOES

CROSS-REFERENCE TO RELATED APPLICATION

This is a continuation-in-part of application Ser. No. 616,283, filed on June 1, 1984, now abandoned and is of common assignee with application Ser. No. 616,283.

BACKGROUND OF THE INVENTION

1. Field of the Invention

The invention relates to techniques for obtaining an image from nuclear magnetic resonance (NMR) data. More specifically, the invention relates to techniques for applying pulses to an object to obtain a series of NMR echoes, which may then be processed and transformed, such as by a Fourier transform, to obtain an image.

2. Description of the Prior Art

The application of the Fourier transform to NMR imaging was demonstrated by A. Kumar, D. Welti, and R. R. Ernst. "NMR Fourier Zeugmatography", *Journal of Magnetic Resonance* 18 (1975), pp. 69–83. U.S. Pat. No. 4,070,611, issued Jan. 24, 1978 to R. R. Ernst, is related to that article and discloses a technique for NMR Fourier imaging in which a series of measurements are taken, each based on a single "Free Induction Decay" signal (FID). The sampled FID's are then stored and processed to obtain an image. The processing includes the use of a computational algorithm approximating the Fourier transform, such as the "Fast Fourier Transform" (FFT). The process may also include arranging a series of FID's, each FID being obtained separately.

U.S. Pat. No. 4,290,019, issued Sept. 19, 1981 to J. M. S. Hutchison et al., discloses another technique for NMR Fourier imaging. This technique includes the application of a sequence of gradient fields and high frequency pulses to obtain a spin echo of the FID. After an echo is obtained, the atoms being imaged are permitted to relax before the sequence is repeated to obtain another echo. The echoes are processed to obtain an image, and the processing includes Fourier transformation.

Other NMR Fourier imaging techniques have been proposed. For example, U.S. Pat. No. 4,319,190, issued Mar. 9, 1982 to T. R. Brown, discloses a technique in which the FID is sampled and stored for subsequent transformation to obtain a chemical shift image.

These prior art NMR Fourier imaging techniques have demonstrated that Fourier imaging can be applied to NMR data. It would be advantageous, however, to provide NMR Fourier imaging techniques which would produce images with improved contrast. In addition, it would be advantageous to provide NMR Fourier imaging techniques in which the data acquisition times are shortened, by reducing the need for additional signal averaging.

SUMMARY OF THE INVENTION

The invention provides NMR Fourier imaging techniques with more sensitive data acquisition and increased image contrast between different types of tissue. The invention is based on the discovery that sensitive data acquisition and increased image contrast can be obtained in NMR Fourier imaging by applying a pulse and gradient switching sequence which produces a series of echoes of each FID. These echoes can be combined into a data set which is then transformed into the image.

In order to perform NMR Fourier imaging, it is necessary to obtain both amplitude and phase information from the object being imaged. The invention is based on the discovery of a method of adding echoes together which preserves all phase information, so that some or all of a series of echoes may be combined without loss of amplitude or phase information. In addition, the invention is based on the discovery of a pulse and gradient switching sequence which preserves the phase information despite errors which result from the application of non-ideal pulses. Furthermore, a pulse and gradient switching sequence has been discovered which provides a series of FID echoes whose base line components cancel when added together, eliminating an undersirable artifact.

The method of the invention thus includes applying a sequence of stimulating signals, the pulse and gradient switching sequence, to the object to be imaged to produce a series of echoes. The echoes are then combined to obtain a data set, and the data set is then transformed into an NMR image of the object.

Similarly, the apparatus of the invention includes means for applying stimulating signals to an object, the applying means being operable for applying the pulse and gradient switching sequence which produces a plurality of echoes. In addition, the apparatus includes combining means for combining the echoes to obtain a combined data set and transforming means for transforming the combined data set into an NMR image of the object.

The sequence of stimulating signals which is applied preferably includes an excitation pulse such as a 90° radio frequency (rf) pulse, which rotates the resonant nuclei in the object through 90°. This pulse is then followed by a series of refocusing pulses which will be 180° rf pulses, each of which rotates the nuclei through 180°. As noted above, the phase error introduced by the pulses is compensated if the excitation and refocusing pulses follow a specific sequence.

The specific pulse and gradient switching sequence may be described in terms of the axes along which the pulses and gradients are applied. The axis along which the constant magnetic field is applied is generally designated the Z axis, and each plane perpendicular to that axis will have a corresponding X axis and Y axis. For purposes of applying pulses, the X and Y axes are not stationary, however, but are rotating in a frame of reference known as the "rotating frame", which rotates at the nuclear spin resonant frequency. Therefore, the pulses and spin magnetizations which are applied along the X and Y axes in the following discussion are actually applied in the rotating frame of reference. This means that the envelope of the given signal is at the nuclear spin resonant frequency, with its phase determined according to the axis along which it is applied. A signal applied along the Y axis will accordingly be 90° out of phase with a signal applied along the X axis.

For example, if the initial excitation pulse is a 90° rf pulse applied along the Y axis, the compensating sequence of refocusing pulses according to the invention can be a series of 180° rf pulses applied in groups of 4 pulses along the positive X and Y axes in the following order: +X, +Y, +X, +Y. In this sequence, the pulses are applied alternatively along the X and Y axes.

If a sequence of stimulating signals like that above is applied, a series of groups of four echoes will be produced. Within each group of four consecutive echoes, two signals will have positive real parts and two will have negative real parts. Similarly, two signals will have positive imaginary parts and two will have negative imaginary parts. As a result, the echoes in each group may be combined to cancel any zero frequency or baseline components, which would otherwise produce an undesirable artifact.

The echoes may be combined by coherent addition. For this purpose, each echo may be analyzed into an in-phase magnetization component which has the same phase as the initial FID resulting from the excitation pulse and an out-of-phase component which is 90° out of phase from the initial FID. The presence of the two components results from the application of phase encoding gradients, so that both components must be preserved in order to preserve the phase information. Therefore, the coherent addition of the echoes requires that both the in-phase components and the out-of-phase components may be added without cancellation to produce combined in-phase and out-of-phase components.

The process of coherent addition may be illustrated in terms of the pulse sequence described above. In this sequence, the second of the echoes being added has an in-phase component which refocuses with inverted phase from that of the first echo, while its out-of-phase component refocuses with the same phase. Therefore, the first and second echoes may be coherently added after reversing the time axis of the second echo, multiplying it by −1 and taking its complex conjugate. As a result, each component of the second echo will be of the same sign as the corresponding component of the first, and the two echoes can be added together without cancelling. Alternatively, alternate echoes may be time reversed and all of the even echoes may be added to form another. In this case, the data set formed from the even echoes will contain information about spatial frequency from the positive phase encoding gradient, while the data set formed from the odd echoes will contain information about spatial frequency from the negative phase encoding gradient.

The echoes will be transformed, before or after coherent adding, to obtain a data set encoded according to spatial frequency. This transform may be a Fourier transform or other similar transform, such as the FFT. In general, as used herein, the terms "Fourier transform" and "transform" refer not only to the Fourier transform in its continuous and discrete forms, but also other similar transforms which depend on phase information, including digital approximations to the Fourier transform such as the FFT and the Hadamard transform. More generally, such a transform will be referred to herein as a "phase-dependent transform".

When the data set encoded according to spatial frequency has been completed, it may then be transformed to provide a spatial image of the object. This transformation may be in two or three dimensions, for example. Because the echoes are combined to form the data set, the resulting image has substantially better contrast than with the prior art techniques.

The method and apparatus of the present invention may reduce data acquisition time for NMR Fourier imaging. Rather than taking several separate FID measurements for signal averaging, as described above in relation to the prior art, the invention makes it possible to obtain several echoes from a single excitation. This is possible because the real spin-spin relaxation time, $T_2$, following an excitation is typically much longer than the effective relaxation time, $T_2^*$, of each echo. As a result, several echoes can be measured after each excitation and combined to obtain significantly greater sensitivity.

Other objects, features and advantages of the invention will be apparent from the following description, together with the accompanying drawings and the appended claims.

DETAILED DESCRIPTION OF THE PREFERRED EMBODIMENTS

I. General Description

The invention provides a method and apparatus for generating an NMR image of an object. The general features of the invention can be understood from FIGS. 1 and 2A.

Figure 1:
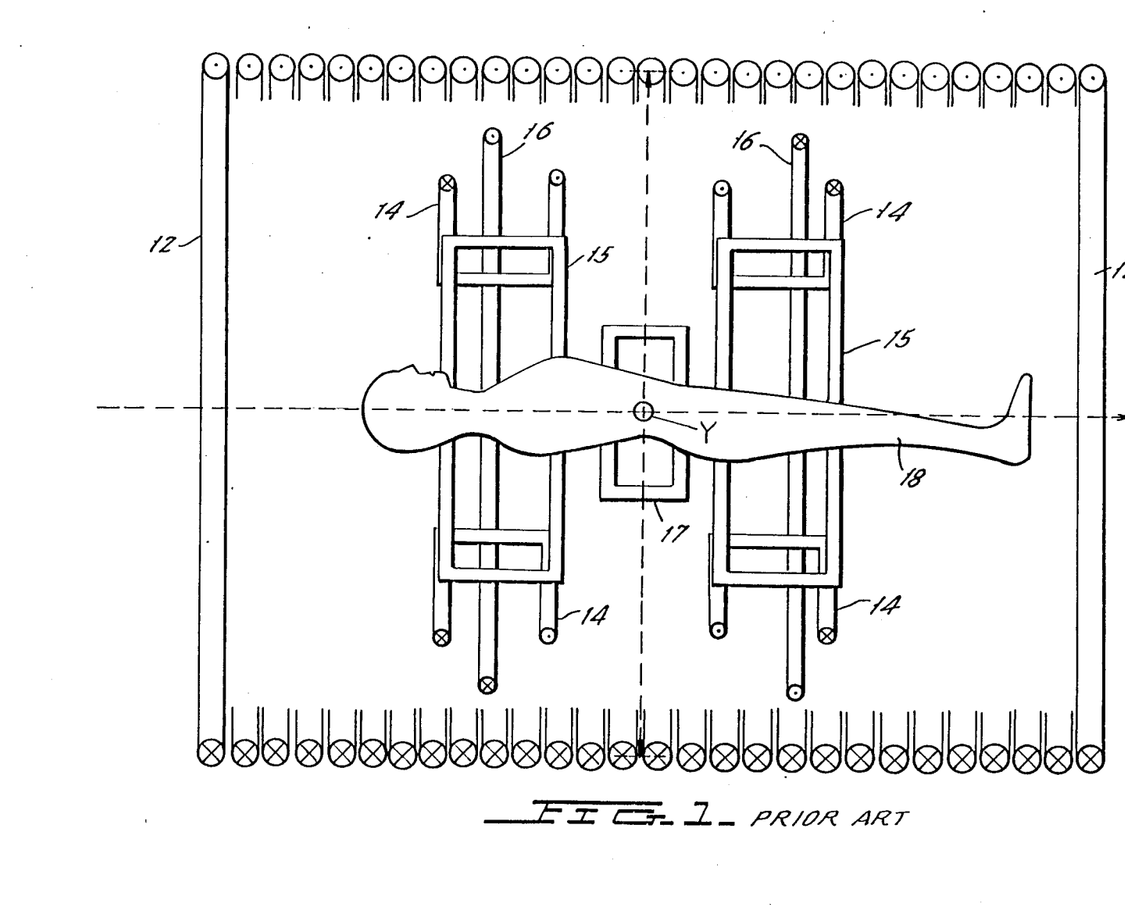
FIG. 1 is a cross sectional view of an arrangement of NMR gradient and rf coils around a subject.

FIG. 1 shows gradient and radio frequency (rf) coils mounted in relation to a human body for imaging. Magnetic coils 10 are oriented in relation to X, Y and Z laboratory axes, which are stationary. Static coil 12 is a solenoidal magnet which will conduct a current to generate a static, uniform magnetic field B along the Z axis, surrounding body 18. Gradient coils 14, 15 and 16 are arranged to provide a gradient field combining components $G_x$, $G_y$ and $G_z$ in the respective X, Y and Z directions. In contrast, rf coil 17 is tuned to the resonant frequency of the substance being imaged. Therefore, rf coil 17 may operate both to provide rf pulses and to detect rf signals from body 18. These signals may then be processed to provide information about body 18, such as an image.

Figure 2A:
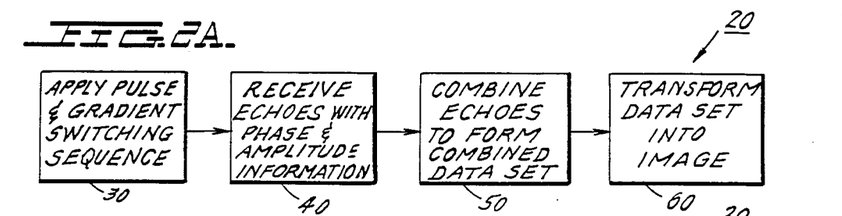
FIG. 2A is a functional block diagram showing the basic operations of NMR Fourier imaging according to the invention.

FIG. 2A is a functional block diagram showing the basic operations of NMR Fourier imaging 20 according to the invention. Block 30 illustrates that the first operation is to apply the pulse and gradient switching sequence. The gradients are applied using gradient coils 14, 15, 16 as shown in FIG. 1, while the pulses are applied using rf coil 17. As shown in block 40, if the sequence of pulses and gradients is appropriate, rf coil 17 will receive echoes containing both phase and amplitude information.

When the echoes have been received as indicated in block 40, they may be combined to form a combined data set, as shown in block 50. This process of combining the echoes must similarly be performed in a manner which preserves the phase information, so that the data set can then be transformed into an image, as shown in block 60.

As can be seen from the above discussion, the pulse and gradient switching sequence applied in block 30 is an important factor in determining whether the subsequent steps of the invention will lead to a high-quality image. As discussed in detail below, the invention provides a pulse and gradient switching sequence which is effective to preserve the phase information and to provide sequences of echoes which can be readily combined without loss of phase information.

II. Pulse and Gradient Switching Sequence

Figure 2B:
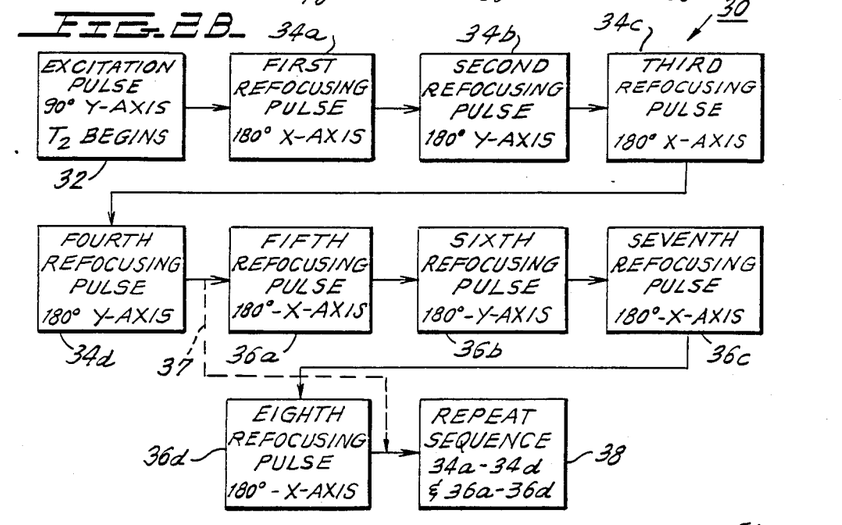
FIG. 2B is a flow chart showing the basic steps of a pulse and gradient switching sequence of the invention.
Figure 3A:
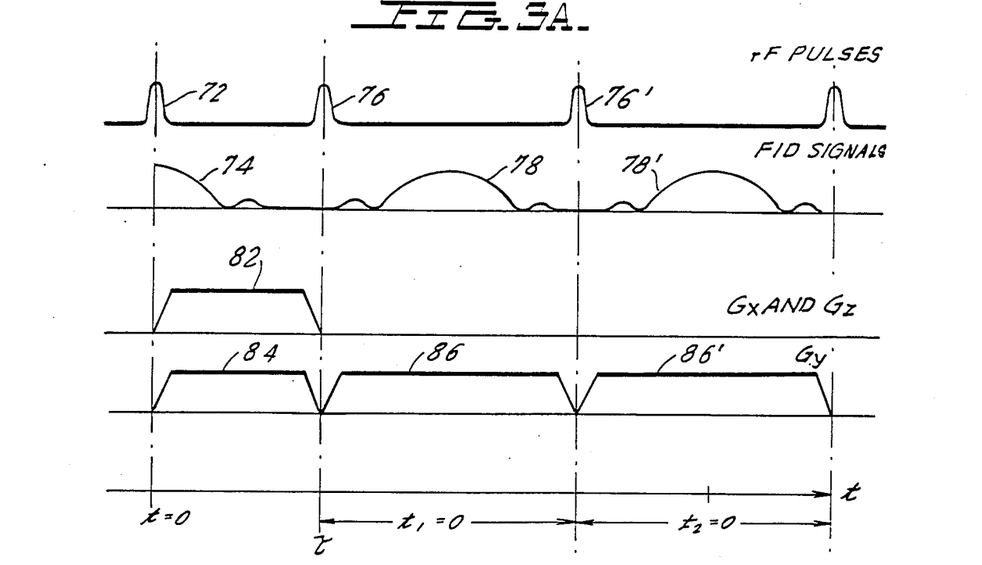
FIG. 3A is a timing diagram of a pulse and gradient switching sequence according to the invention.
Figure 3B:
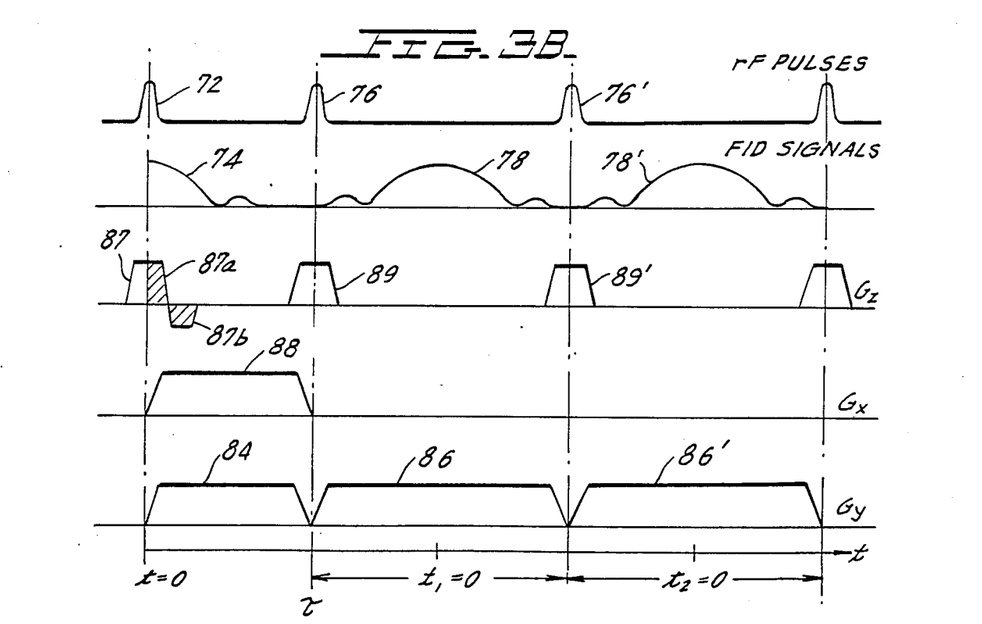
FIG. 3B is a timing diagram of an alternative embodiment of the pulse and gradient switching sequence of the invention.

The pulse and gradient switching sequence of the invention provides a series of NMR echoes which can be combined into a single data set without loss of phase information. FIG. 2B is a flow chart showing the basic steps of a pulse and gradient switching sequence according to the invention, while FIGS. 3A and 3B are timing diagrams of two different pulse and gradient switching sequences according to the invention.

In order to produce echoes, the pulse and gradient switching sequence must stimulate a resonance whose real decay time is longer than its effective decay time. In other words, even though each resonant atom may decay relatively slowly to the steady state, the observable magnetization from a combination of atoms in the object being imaged appears to decay relatively rapidly. For example, a spin-spin relaxation time, $T_2$, of each atom may be substantially longer than the effective spin-spin relaxation time, $T_2^*$, observed for a part of the object containing many atoms. Even though the resonance of each individual atom will decay with a time constant of $T_2$, the measurable decay will have a much shorter time constant, $T_2^*$, unless the atoms can somehow be refocused to produce a measurable signal.

As shown in FIG. 2B, the pulse and gradient switching sequence 30 of the invention begins with a 90° rf excitation pulse along the Y axis, shown in block 32. This excitation pulse begins the $T_2$ decay of each atom's resonance. It also begins an initial $T_2^*$ decay of the composite of the atoms. This can be seen in FIG. 3A, in which the excitation pulse 72 is followed by an initial $T_2^*$ decay 74.

The first of the echoes is produced by the first refocusing pulse, shown in block 34a in FIG. 2B. The mechanism by which the refocusing pulses produce echoes will be discussed in greater detail below in relation to FIGS. 10 and 11. As indicated in FIG. 2B, however, if the excitation pulse is a 90° pulse along the positive Y axis, the first refocusing pulse of pulse and gradient switching sequence 30 will be a 180° rf pulse along the X axis. This pulse serves to reflect the spin magnetization vectors around the X axis, so that as the $T_2$ decay continues, the magnetization is refocused to form a spin echo decaying according to $T_2^*$. As shown in FIG. 3A, the first refocusing pulse 76 will result in an echo 78 centered about the point at which the axes of the atoms are aligned approximately as they were after the excitation pulse 72. As can be seen in FIG. 3A, echo 78 rises to its peak along a wave form which resembles a mirror image of the initial $T_2^*$ decay 74. Echo 78 then decays with a time constant of $T_2^*$, again resembling the wave form of initial $T_2^*$ decay 74.

At this point, a second refocusing pulse, a 180° rf pulse along the Y axis is applied, as shown in block 34b of FIG. 2B. The effect of this pulse is to reflect the spin axes of the atoms about the Y axis, resulting in another echo. As shown in FIG. 3A, the second refocusing pulse 76' results in a second echo 78', closely resembling the first echo 78.

In addition to refocusing pulses, other techniques may be used to form echoes. For example, echoes can be formed by reversing the gradient along the Y axis $G_y$. In other words, rather than applying a series of positive gradients 86 and 86', as shown in FIG. 3A, the sign of the gradients may be alternately positive and negative. This results in a series of echoes which can be coherently added, but which suffer from progressive dephasing as a result of phase error. Therefore, this technique is not as desirable as the use of the pulse and gradient switching sequence shown in FIG. 3A.

Although the second echo 78' shown in FIG. 3A closely resembles the first echo 78, the reflection of the spin axes of the atoms around the Y axis causes the refocusing to be reflected about the Y axis as well. This process is repeated for each refocusing pulse and has the effect of compensating for phase error introduced by each of the pulses. Pulse and gradient switching sequence 30 continues with a third refocusing pulse, as shown in block 34c in FIG. 2B. This third refocusing pulse is a 180° rf pulse along the X axis. A fourth refocusing pulse is applied as shown in block 34d in the form of a 180° rf pulse along the Y axis. The result of the first through fourth refocusing pulses 34a–34d will be to return the spin axes of the atoms to the position prior to the first refocusing pulse 76. In addition, the phase error introduced by each of the refocusing pulses will be compensated.

The pulse and gradient switching sequence 30 of the invention may include a series of refocusing pulses along the negative X and Y axes, as shown in FIG. 2B. The fifth refocusing pulse, shown in block 36a, is a 180° rf pulse along the negative X axis, and the sixth refocusing pulse, shown in block 36b, is a 180° rf pulse along the Y axis. The seventh and eighth refocusing pulses shown in blocks 36c and 36d are also 180° rf pulses along the negative X and Y axes. Therefore, the fifth through eighth refocusing pulses compensate pulse phase error in the same manner as the first through fourth refocusing pulses shown in blocks 34a–34d. It is preferred, however, to utilize a sequence of refocusing pulses not including pulses 36a–36d along the negative X and Y axes; e.g., pulses 34a–34d, which are directed along the positive X and Y axes.

As indicated in block 38 of FIG. 2B, the sequence of refocusing pulses in blocks 34a–34d and 36a–36d (if included) can be repeated in the order given to obtain additional echoes which are compensated. Dashed line arrow 37, which bypasses blocks 36a–36d, represents the preferred sequence of pulses. The number of refocusing pulses possible will depend on the ratio between $T_2$ and $T_2^*$, discussed in greater detail below. If that ratio is quite large, a large number of echoes may be obtained by repeating the sequence of refocusing pulses several times. It is not necessary, however, to repeat the entire sequence of pulses to obtain the compensation of phase error, as will be seen from FIG. 4A, discussed below.

Figure 4A:
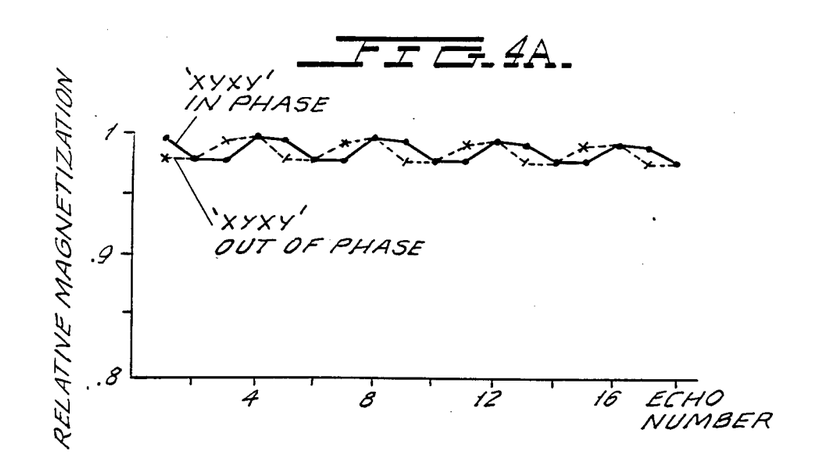
FIGS. 4A and 4B are graphs which compare the pulse error compensation resulting from the pulse and gradient switching sequence of FIG. 3A with the pulse error which would result from the use of a prior art pulse sequence.
Figure 4B:
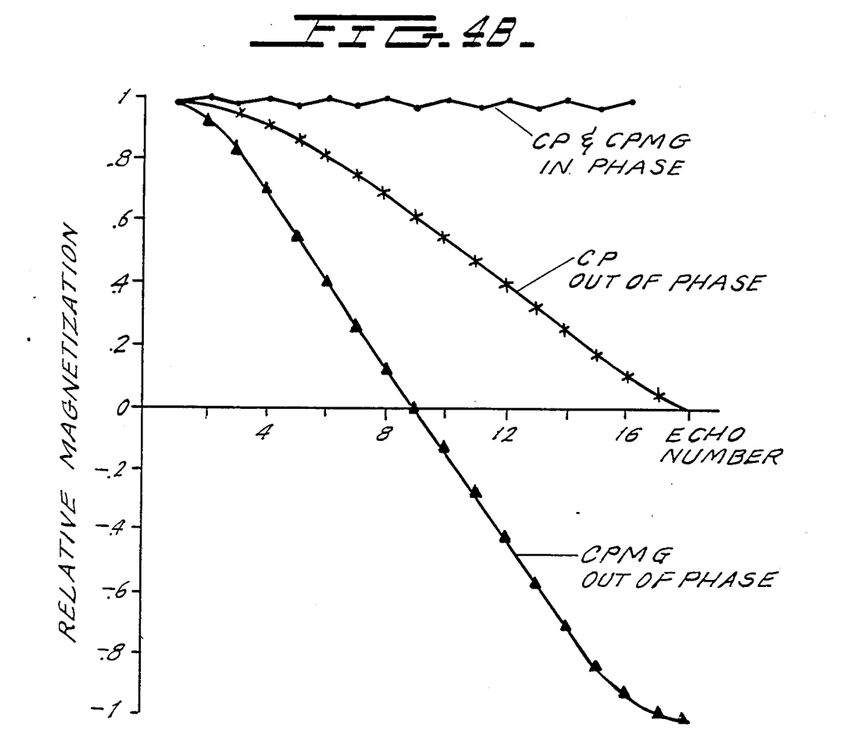

The manner in which pulse phase error is compensated is shown in FIGS. 4A and 4B, which are based on the use of pulses 34a–34d and any repitition thereof at block 38. FIGS. 4A and 4B compare the phase error after each pulse of the pulse and switching sequence 30 (the XYXY sequence) with the error after each pulse of the Carr-Purcell sequence (CP) and the Carr-Purcell-Meiboom-Gill sequence (CPMG) used in some types of NMR measurement to obtain spin echoes. S. Meiboom and D. Gill, 29 Rev. Sci. Instruments 688 (1958) discuss these sequences. FIG. 4A shows the variation in amplitude of the relative magnetization of the in-phase and out-of-phase components of the echoes resulting from the pulse and gradient switching sequence 30 of the invention. FIG. 4B, on the other hand, shows the variation in amplitude of the in-phase and out-of-phase components of the echoes resulting from the CP and CPMG pulse sequences.

In both FIGS. 4A and 4B, it is assumed that each refocusing pulse, rather than being a full 180° pulse, is an effective pulse of 170°, and therefore introduces an error of 10° per pulse. This error may result from inaccurate setting or other causes. As shown in FIG. 4A, both the in-phase and out-of-phase components of the echoes are fully compensated for the error after each group of four spin echoes. In addition, both components have values close to the full relative magnetization even for those echoes which are not fully compensated, with the maximum loss of signal less than 8%. In contrast, as shown in FIG. 4B, the in-phase components of the echoes resulting from the CP and CPMG pulse sequences are compensated, but the out-of-phase components deteriorate rapidly. The in-phase CP and CPMG components are very well compensated, with a loss of 1.5% on alternate refocusing pulses. The out-of-phase CP and CPMG components, on the other hand, show no substantial compensation, so that the amplitude varies widely. For the CPMG sequence, after nine refocusing pulses, each in error by 10°, the amplitude goes to zero, indicating that the full 90° of error is uncompensated. As a result, the phase information is lost with the CP and CPMG pulse sequences.

As described above, the refocusing pulses of the invention are applied along X and Y axes in the rotating frame of reference. In addition, as shown in FIGS. 3A and 3B, gradient fields along the X, Y and Z axes in the laboratory frame of reference may also be applied for spatial encoding of the NMR data. In addition, FIGS. 3A and 3B show in greater detail the timing of the pulses discussed above.

As shown in FIG. 3A, gradients 82 and 84 are applied after the excitation pulse 72. Gradient 82 may include both $G_x$ and $G_z$ components. These components of gradient 82 are applied only during the evolution period between initial excitation pulse 72 and the first refocusing pulse 76. During this evolution, the spin axes of the atoms begin in a plane perpendicular to the Y axis and move toward the Y axes at a rate determined by gradient 84 which has a compenent $G_y$. Gradient 82 performs a phase encoding function, which encodes the phase of the magnetization in the X-Z plane according to the spatial location along the X and Z axes in the laboratory frame of reference. The amount of phase encoding depends on the strength of the components of the field gradient 82 and the location of the spin in the X-Z plane. The $G_x$ and $G_z$ components of gradient 82 may be applied successively.

The $G_y$ component of gradient 84 is necessary because refocusing gradients 86 and 86' also include $G_y$ components. For correct refocusing, gradient 84 and 86 must satisfy the condition expressed in the following equation:

$$\int_{t=0}^{T} t\, G_y\, dt = \int_{t_1 = -\tau}^{0} t_1\, G_y\, dt_1 \qquad (1)$$

In equation (1), t represents the time from excitation pulse 72, while $t_1$ represents the time from the peak of the first echo 78. In FIGS. 3A and 3B, $t_1$ equals $t-2\tau$ and $t_2$ equals $t-4\tau$, where $\tau$ represents the time between the excitation pulse 72 and the first refocusing pulse 76. $\tau$ is chosen to provide an optimal evolution, and the time between refocusing pulses will be $2\tau$. As a practical matter, the first half of each refocusing gradient 86, 86' is a phase encoding gradient over time, while the second half serves to re-encode the phase of the magnetization along the Y axis. Because of this use of $G_y$ for two purposes, gradient 84 is necessary for encoding before the echoes begin.

In contrast to gradient 82 of FIG. 3A, gradient 88 of FIG. 3B contains only a $G_x$ component. As a result, therefore, the pulse and gradient switching sequence of FIG. 3B does not result in phase encoding in the Z direction. This sequence can be used, however, for two-dimensional imaging, in which a plane transverse to the Z axis is selected by a selective pulse 87 and appropriate refocusing gradients 89 and 89' are applied, all being $G_z$ components. In order to obtain the desired phase of the nuclei along the Z axis, area 87b should equal area 87a. This will return the phase along the Z axis to its value at $t=0$. Other than these differences, the sequence shown in FIG. 3B is the same as that of FIG. 3A.

In the sequences shown in FIGS. 3A and 3B, a single excitation pulse 72 is followed by refocusing pulses, including first refocusing pulse 76 and second refocusing pulse 76'. In order to obtain a complete data set, however, a series of observations must be made, each beginning with an excitation pulse 72 followed by gradient 82 or gradient 88. As noted above, the phase encoding, which may be measured in degrees, depends on the strength of these gradients. Therefore, a series of measurements may be taken using gradients of different strengths to obtain data sets with different amounts of phase encoding. These data sets may then be ordered according to phase encoding to provide a combined data set which is then transformed.

The pulse and gradient switching sequence 30 of the invention provides a series of echoes having specific characteristics. The application of a series of pulse and gradient switching sequences 30 with different degrees of phase encoding will produce a set of echo trains, each of which may be combined to form one or more data sets according to the invention. Before describing how the echoes are combined, however, it is helpful to consider the mathematical characteristics of these echoes.

III. The Characteristics of the Echoes Received

As discussed above in relation to block 40 of FIG. 2A, one basic operation of the invention is to receive echoes having both phase and amplitude information. This information must be preserved during the process of combining the echoes into the data set. Therefore, in order to understand how the echoes are combined, it is necessary to consider the mathematical characteristics of each echo.

In general, we will assume that all of the NMR signals are detected by quadrature detection. A phase sensitive detector, such as a double balanced mixer circuit, may be used, for example, to separate the signal into an in-phase component and an out-of-phase component, as discussed below. It should be noted, however, that the error compensation resulting from pulse and gradient switching sequence 30 does not depend on using quadrature detection.

The signal arising from spins at a location $x_O$, $y_O$, $z_O$ at a time $t_1$ during the first echo can be described as follows:

$$S(t_1, x_O, y_O, z_O) = M_O(\cos(\omega t_1 + \phi) + i \sin(\omega t_1 + \phi))\text{Exp}(-2\tau/t_2^*) \quad (2)$$

In equation (2), the signal is expressed as S, $M_O$ represents the equilibrium magnetization at the point $x_O$, $y_O$, $z_O$, and $\omega$ is equal to the product of the gyromagnetic ratio $\gamma$ with the coordinate $z_O$ and the gradient $G_z$. In addition, $\phi$ is the phase encoding term, given by:

$$\phi = \gamma \left( x_0 \int_{t_1=0}^{\tau} G_x t_1 \, dt_1 + z_0 \int_{t_1=0}^{\tau} G_z t_1 \, dt_1 \right) \quad (3)$$

In order to simplify our discussion, we will treat $M_O$ as being equal to unity and we will ignore the exponential relaxation term in equation 2. Therefore, each signal may be expressed as the sum of a real term and a complex term. Each of these terms, however, will be dependent on the phase encoding term $\phi$, resulting from the successive applications of $G_x$ and $G_z$ as they affect the location $x_O$, $z_O$. The resulting spin packet at the location $x_O$, $y_O$, $z_O$ will be the sum of all spin magnetization arising in a voxel at that position, and the phase of this spin packet may vary over a full 360° or $2\pi$ radians.

For purposes of subsequent discussion, we define two components, signal $S_A$ in which $\phi=0$ and signal $S_B$ in which $\phi=\pi/2$ radians. Signals $S_A$ and $S_B$ are orthogonal, and together are equal to the entire signal S. As noted above, $S_A$ and $S_B$ may be obtained from a phase sensitive detector. Therefore, the signals obtained at the first echo for each of these components will be:

$$S_A(t_1) = \cos(\omega t_1) + i \sin(\omega t_1) \quad (4A)$$

$$S_B(t_1) = -\sin(\omega t_1) + i \cos(\omega t_1) \quad (4B)$$

Figure 10:
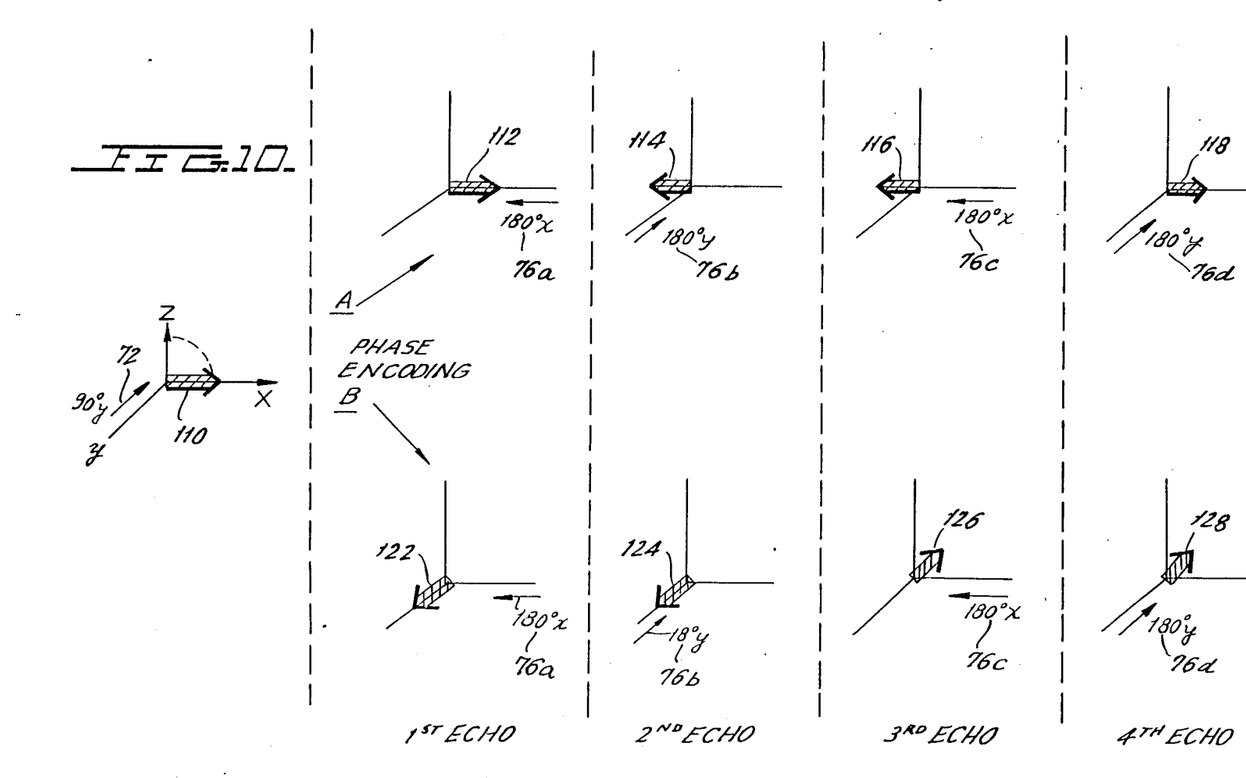
FIG. 10 is a sequence of graphs showing the phases of the components of a series of echoes.

The relation between $S_A$ and $S_B$ can be better understood by referring to FIG. 10, which shows schematically the magnetization resulting from some pulses of pulse and gradient switching sequence 30. As shown at left in FIG. 10, excitation pulse 72, a 90° rf pulse along the Y axis in the rotating frame of reference, causes the magnetization to rotate through 90° from the z axis to the X axis, resulting in initial magnetization 110. As a result of phase encoding, initial magnetization 110 evolves into a form having in-phase component A and out-of-phase component B. As a result of first refocusing pulse 76a, a 180° rf pulse along the X axis, first echo magnetizations 112 and 122 result along the X and Y axes, respectively.

Figure 11:
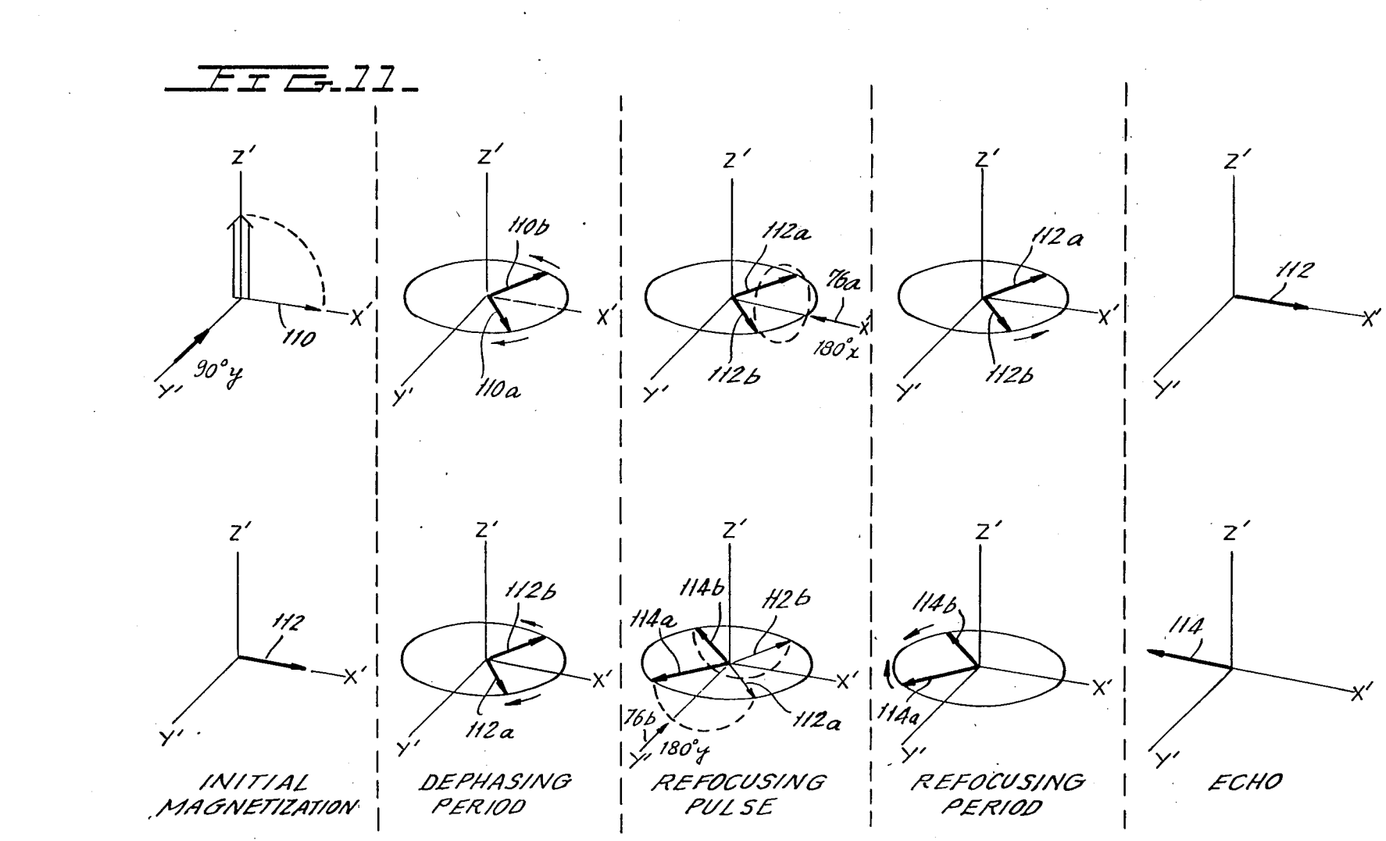
FIG. 11 is a sequence of graphs showing in greater detail the production of the first two echoes.

The formation of first echo magnetization 112 of the in-phase component A is illustrated schematically in the top line of FIG. 11. As in FIG. 10, excitation pulse 72 rotates the magnetization through 90° to form initial magnetization 110. Ignoring the phase encoding process, magnetization 110 will dephase, resulting in initial $T_2^*$ decay 74, shown in FIG. 3A. This dephasing is illustrated in FIG. 11 by two representative spin vectors 110a and 110b which, even though still excited, tend to cancel each other due to their movements in different directions. When refocusing pulse 76a is applied, however, vectors 110a and 110b are reflected about the X axis, creating reflected vectors 112a and 112b. Reflected vectors 112a and 112b then refocus by converging to form first echo magnetization 112.

The second echo may similarly be described by considering that the second refocusing pulse 76b, a 180° rf pulse along the Y axis, rotates all of the spins about the Y axis, assuming a coordinate system in which the X axis is equivalent to $\phi=0$ in the rotating frame of reference. Therefore, the spins having $\phi=0$, the in-phase component A, will refocus with inverted phase as second echo magnetization 114. This is illustrated schematically on the second line of FIG. 11, which begins with the first echo magnetization 112 which resulted from the first line of FIG. 11. Magnetization 112 will dephase, illustrated in FIG. 11 by two representative spin vectors 112a and 112b. When refocusing pulse 76B is applied, vectors 112a and 112b are reflected about the Y axis, creating reflected vectors 114a and 114b. Reflected vectors 114a and 114b then refocus by converging to form second echo magnetization 114.

As shown in FIG. 11, the in-phase component A, including the spins having $\phi=0$, will refocus as second echo magnetization 114, having a sign opposite that of first echo magnetization 112. In other words, the in-phase component refocuses with inverted phase. On the other hand, the spins having $\phi=\pi/2$ radians, the out-of-phase component B, will refocus with the same phase to form second echo magnetization 124. Therefore, the second echo can be described as:

$$S_A(t_2) = -\cos(\omega t_2) - i \sin(\omega t_2) \quad (5A)$$

$$S_B(t_2) = -\sin(\omega t_2) + i \cos(\omega t_2) \quad (5B)$$

Similarly, third refocusing pulse 76c, a 180° rf pulse along the X axis, will invert the phase of only the out-of-phase component, as third echo magnetization 126, leaving the phase of third echo magnetization 116 the same for the in-phase component. Fourth refocusing pulse 76d, a 180° rf pulse along the Y axis, will invert the in-phase fourth echo magnetization 118 but not the out-of-phase magnetization 128. Thus it can be seen graphically from FIG. 10 that the components A and B of the fourth echo will have the same phase relation to the components of the third echo as the components of the second echo have to the first echo. In general, the echo from each even-numbered refocusing pulse of pulse and gradient switching sequence 30 will have this same relation to the preceding odd-numbered echo, so that we may generally treat equations 4A and 4B as describing the odd echoes and equations 5A and 5B as describing the even echoes.

From these basic expressions for the in-phase and out-of-phase components of the odd and even echoes, the process by which the echoes are combined into the data set by coherent addition may now be understood.

IV. Coherent Adding of Echoes

Figure 2C:
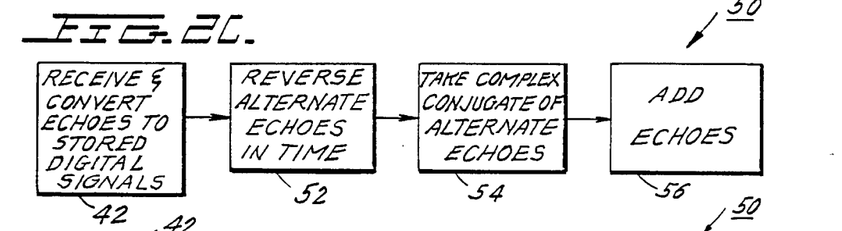
FIG. 2C is a detailed flow chart showing the embodiment of coherent adding of echoes according to the invention.
Figure 2D:
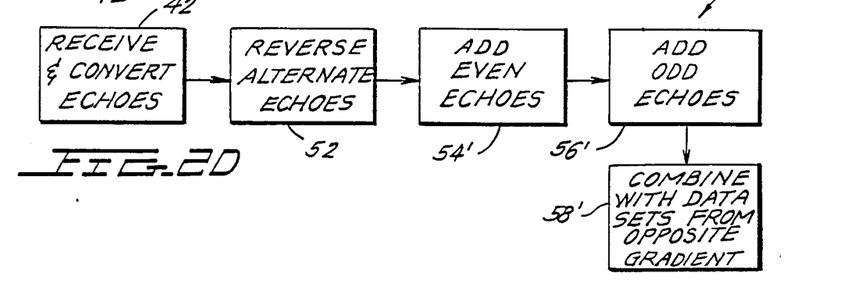
FIG. 2D is a detailed flow chart showing an alternative embodiment of coherent adding of echoes according to the invention.

As discussed above, each echo received as a result of the pulse and gradient switching sequence 30 contains both amplitude and phase information which can be represented by the real and imaginary components of a complex function. FIGS. 2C and 2D are flow charts showing two ways in which these echoes may be coherently added according to the invention. In both cases, the coherent addition results in a data set in which both phase and amplitude information are present.

As shown in FIG. 2C, the process begins with block 42, in which the echoes are received and converted into stored digital signals. This may be done, for example, by a phase-sensitive detector followed by an analog-to-digital converter. The result will preferably be a group of measurements for the in-phase and out-of-phase components similar to those in equations 4 and 5, above. As can be seen, however, if the out-of-phase components, represented in equations 4B and 5B, are added directly, cancellation will occur because of differences in sign. Therefore, it is necessary to modify at least one of the echoes to make the signs compatible. According to the embodiment shown in FIG. 2C, this can be done by time reversing the alternate echoes, as shown in block 52. If we treat the second echo as the echo to be reversed in time and as a negative echo, we may rewrite equations 5A and 5B by replacing $t_2$ with $-t_2$ and multiplying by $-1$ as follows:

$$S_A(t_2) = \cos(\omega t_2) - i \sin(\omega t_2) \quad (6A)$$

$$S_B(t_2) = -\sin(\omega t_2) - i \cos(\omega t_2) \quad (6B)$$

The next step, shown in block 54, is to take the complex conjugate of the alternate echoes, which yields:

$$S_A(t_2) = \cos(\omega t_2) + i \sin(\omega t_2) \quad (7A)$$

$$S_B(t_2) = -\sin(\omega t_2) + i \cos(\omega t_2) \quad (7B)$$

As can be seen by comparing equations 7A and 7B with equations 4A and 4B, the signs of the terms are now the same for the first echo and the second echo, and the two data sets can be added together, term by term. Furthermore, subsequent echoes can be treated in the same manner such that all odd numbered echoes are treated alike and all even numbered echoes are also treated alike. Therefore, the final step of this embodiment is to add the echoes as shown in block 56 of FIG. 2C.

Since the time reversal of block 52 and the complex conjugate of block 54 do not affect the sign of the real components, the addition of the echoes in block 56 also results in a cancellation of any existing zero frequency or baseline components. When using the preferred pulse and gradient switching sequence 30 of the invention, the real parts of the complex data set will be summed with the signs $(+, -, -, +)$ for each group of four echoes. Since the complex conjugate operation of block 54 changes the sign of imaginary zero frequency components, they will be summed with the signs $(+, +, -, -)$, which will also result in cancellation of the baseline offsets. Therefore, the use of the pulse and gradient switching sequence 30 with coherent addition 50 results in cancellation of baseline offsets.

Figure 5A:
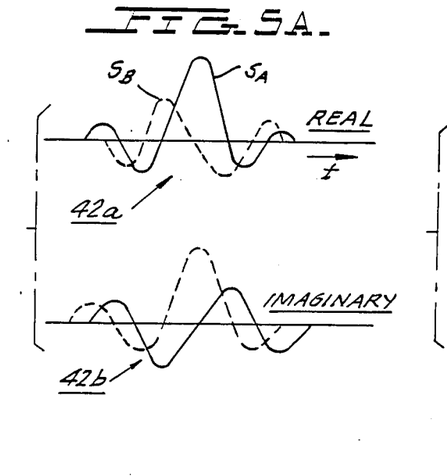
FIG. 5A is a graphical illustration of the real and imaginary parts of an odd echo.
Figure 5B:
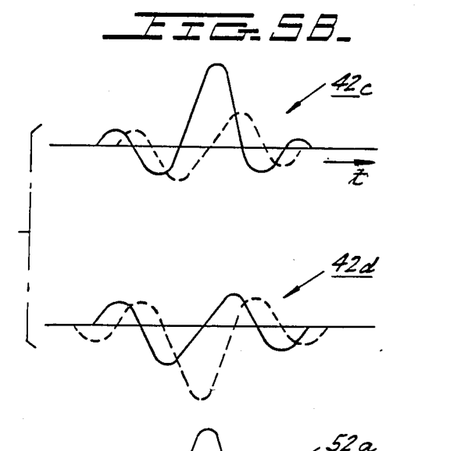
FIG. 5B is a graphical illustration like that of FIG. 5A for an even echo.
Figure 5C:
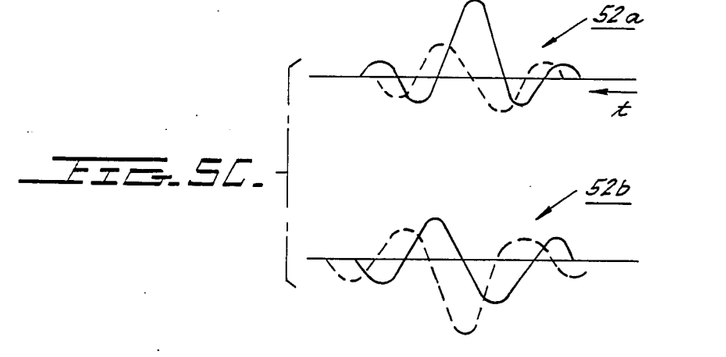
FIG. 5C is a graphical illustration of the time reversal of the waveform of FIG. 5B.
Figure 5D:
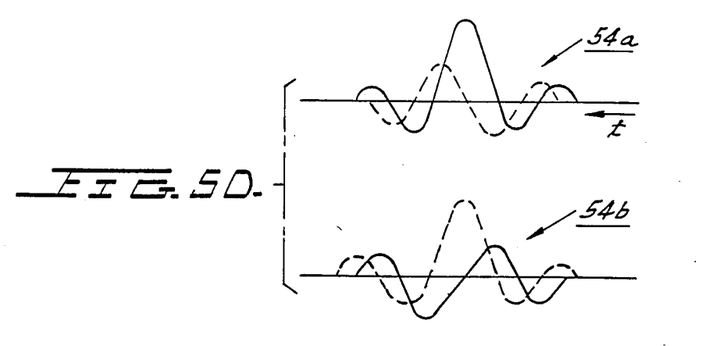
FIG. 5D is a graphical illustration of the complex conjugate of the waveform of FIG. 5C.

FIGS. 5A–5D illustrate graphically the process of coherent addition according to FIG. 2C. In each part of FIGS. 5A–5D, the in-phase signal $S_A$ is shown in solid line, while the out-of-phase signal $S_B$ is shown in dashed line. FIG. 5A shows real components 42a and imaginary components 42b of an odd echo, each with an arbitrary illustrative waveshape. FIG. 5B shows real components 42c and imaginary components 42d of an even echo, which will bear a characteristic relation to the components 42a and 42b of the odd echo. FIG. 5C shows the even echo of FIG. 5B after time reversal, so that real components 52a are the time reversal of components 42c and imaginary components 52b are the time reversal of components 42d. FIG. 5D shows the even echo after taking the complex conjugate of the components of FIG. 5C, so that real components 54a are the same as components 52a, while imaginary components 54b are opposite in sign from components 52b. As can be seen by comparing FIGS. 5A and 5D, the real components 42a and 54a are similar in shape while imaginary components 42b and 54b are also similar, illustrating graphically how the odd and even echoes can be added without cancellation.

FIG. 3A shows gradient 82 as a combination of positive amplitudes, for illustrative purposes. As a practical matter, however, components $G_x$ and $G_z$ will be applied for all amplitudes between their positive and negative maxima $+G_x$max to $-G_x$max and $+G_z$max to $-G_z$max. If we take a general case in which $\phi' = -\phi$ in equation 3, substituting this value into equation 2 results in different in-phase and out-of-phase components than set forth above. For the in-phase component, $\phi$ remains equal to zero, but for the out-of-phase component, $\phi$ is now equal to $-\pi/2$. Therefore, the first echo may be expressed as:

$$S'_A(t_1) = \cos(\omega t_1) + i \sin(\omega t_1) \quad (8A)$$

$$S'_B(t_1) = \sin(\omega t_1) - i \cos(\omega t_1) \quad (8B)$$

The second echo is also modified and becomes:

$$S'_A(t_2) = \cos(\omega t_2) + i \sin(\omega t_2) \quad (9A)$$

$$S'_B(t_2) = -\sin(\omega t_2) + i \cos(\omega t_2) \quad (9B)$$

Comparing equations 9A and 9B with equations 4A and 4B, it is apparent that the second echo obtained from the negative application of the spatial encoding gradient is identical, except for relaxation effects, to the first echo from the positive application of the same spatial encoding gradient. Therefore, these two data sets may be added together without out any additional data processing. Similarly, comparing equations 8A and 8B with equations 5A and 5B, it is apparent that the first echo from the negative spatial encoding gradient may be added to the second echo from the positive encoding gradient without additional data processing.

FIG. 2D shows an alternative method of coherently adding the echoes to form data sets which follows from the above discussion. In this method, the echoes are received and converted to stored digital signals in block 42, in the same manner as in FIG. 2C. In addition, alternate echoes from each pulse and gradient switching sequence 30 are time reversed in block 52, a step which conveniently changes the sign of the real term in equations 4B and 9B. This step is also the same as in FIG. 2C. Then, in block 54', all of the even echoes from each pulse and gradient switching sequence 30 are added together to obtain the spatial frequency information for one data set. Similarly, in block 56', all of the odd echoes are added to provide a second data sets. Then, in block 58', the first and second data sets are combined with the data sets from the opposite phase encoding gradient. More specifically, the first data set from each phase encoding gradient will be added to the second data set from the phase encoding gradient of opposite sign, resulting in two combined data sets.

Figure 6:
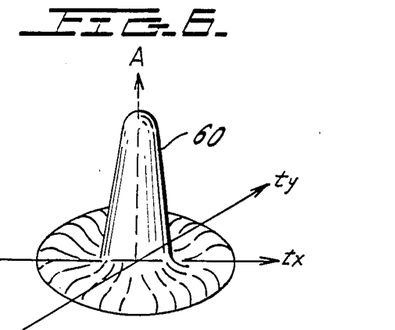
FIG. 6 is a graphical illustration of a two-dimensional data set derived from the coherent addition of echoes.
Figure 7:
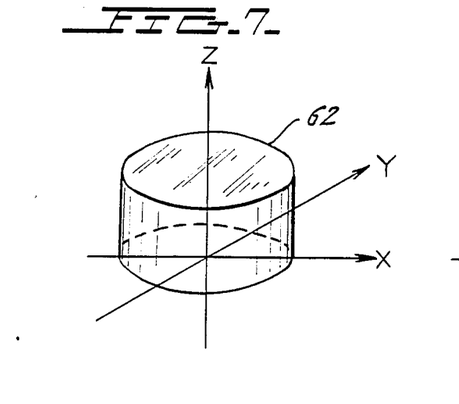
FIG. 7 is a simplified representation of an image which would result from the transformation of the data set shown in FIG. 6.

Either before or after the coherent addition of the echoes, a Fourier transformation is performed to convert from the time domain to the frequency domain. As a result, the data sets can be ordered according to the phase encoding into a combined data set. An example of such a combined data set 60 is shown graphically in FIG. 6. As noted above, the Fourier transformation of this combined data set will then produce a spatial image of the object under investigation. FIG. 7 shows a simplified representation of an image 62 which would result from taking the Fourier transform of the data set 60 shown in FIG. 6.

Having described the method of the invention, we turn now to the apparatus used to perform the method.

V. NMR Fourier Imaging Apparatus

Figure 8:
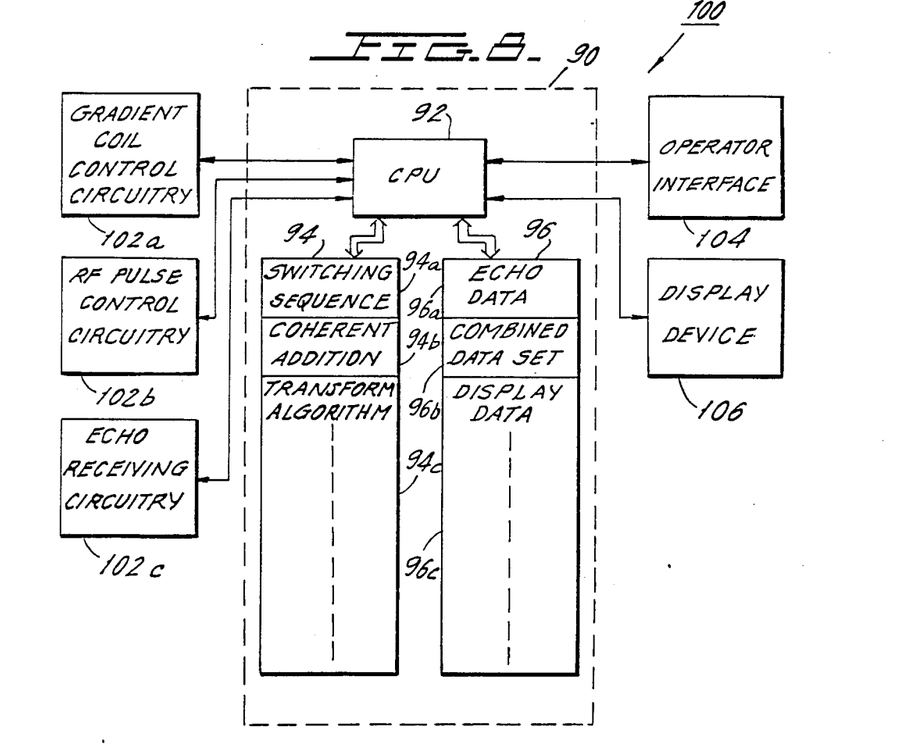
FIG. 8 is a block diagram of the apparatus of the invention.

FIG. 8 shows a block diagram of the apparatus of the invention which may be used for performing NMR Fourier imaging.

NMR Fourier imaging apparatus 100 includes control and processing circuitry 90, which may typically be a programmed digital computer. In order to provide the pulse and gradient control sequence 30, computer 90 will be connected to gradient coil control circuitry 102a and rf pulse control circuitry 102b. In addition, computer 90 will be connected to receiving circuitry 102c for receiving the NMR signals and converting them into digital form.

In the simplified block diagram of FIG. 8, computer 90 is represented as including a central processing unit (CPU) 92, program memory 94, and a data memory 96. The operation of the CPU 92 includes sending and receiving appropriate signals from the gradient coil control circuitry 102a, the rf pulse control circuitry 102b and the receiving circuitry 102c. In addition, CPU 92 is connected to an appropriate operator interface 104, which may be a standard operator terminal. Similarly, CPU 92 is connected to a display device 106, which may be a CRT display or any other appropriate display having the necessary degree of resolution.

The operation of CPU 92 will be initiated by appropriate signals from the operator interface 104. In response to those signals, CPU 92 will initiate the pulse and gradient switching sequence 30 in response to the switching sequence program 94a stored in program memory 94. Execution of this program will cause CPU 92 to send signals to gradient coil control circuitry 102a and rf pulse control circuitry 102b to produce the pulse and gradient switching sequence 30. As a result, echoes will be received by receiving circuitry 102c and changed into digital form, as described above. As a part of the switching sequence program 94a, CPU 92 also operates to store the digitized echoes in the echo data memory 96a.

CPU 92 also executes coherent addition program 94b in order to combine each set of echoes into a respective data set stored in combined data set memory 96b. As noted above, the echo data will be Fourier transformed before or after the coherent addition, and this Fourier transformation should be performed as a part of coherent addition program 94b.

When all of the data sets have been stored in combined data set memory 96b, CPU 92 executes transform algorithm 94c in order to obtain the basic image data which is stored in display data memory 96c. The display data may then be read out by CPU 92 to the display device 106 for display to the operator.

In general, the switching sequence program 94a and coherent addition program 94b will perform the steps described above in order to preserve the phase information necessary to perform Fourier imaging. In addition, these programs will preferably conform to the additional design constraints set forth below.

IV. Additional Design Considerations

In order to obtain high quality images, an operator may improve sensitivity by increasing the number of echoes after each of the excitation pulses. The number of echoes can be varied within limitations determined by physical parameters. In addition to the real spin-spin relaxation time, $T_2$, it is useful to define two additional decay constants or transverse relaxation times. $T_2^*$, used above to represent the apparent relaxation time, may be more narrowly defined as the relaxation time which takes into account the additional contribution from local field inhomogeneity over the resolution element or voxel in question. $T_2^{**}$, can then be defined as the relaxation time which takes into account the field inhomogeneity over the whole object within the imaging region. In general, $T_2 > T_2^* > T_2^{**}$.

Based on these definitions, the optimal field gradient will satisfy the following condition:

$$\gamma G \, d \geq 1/\pi T_2^{**} \tag{10}$$

If the field gradient satisfies equation (10), frequency variations due to field inhomogeneity remain within the frequency spread across the resolution element of length d in the direction of the applied field gradient G. In order to sample this frequency, the echo signal should be sampled for a time $t_s$, where:

$$t_s \geq 2 \, T_2^{**} \tag{11}$$

To obtain the best possible signal-to-noise (S/N) ratio, $t_s$ should be as short as possible, and should therefore have a value of twice $T_2^{**}$. This will result in an image which is relatively free of Spatial distortions due to field inhomogeneity.

Even if the above conditions are not met, an acceptable image can be obtained using the Fourier imaging techniques described above, as long as the following condition is met:

$$G \, d \geq 1/\pi T_2^* \tag{12}$$

What this means is that $T_2^*$ places a lower limit on the strength of the field gradient necessary to produce an acceptable image. The image will, however, be spatially distorted due to the effect of field inhomogeneity. This distortion may be acceptable for the particular imaging requirements or, alternatively, the distortion may be corrected by suitable software. Furthermore, the S/N ratio may be improved by reducing the band width over which the NMR signal is received, because the noise power at each point is proportional to the square root of the frequency band at that point. The frequency band, in turn, is the reciprocal of the sampling time $t_s$.

The signal S(M) which can be obtained by summing echoes, keeping all other parameters constant, is given by:

$$S(M) = \int_{m=1}^{M+t_s/2} \int_{t=-t_s/2} \text{Exp}(-t/T_2^{**})\text{Exp}(-(mt_s+t)/T_2)dt\,dm \quad (13)$$

This equation neglects the pulse lengths and assumes that the time between the excitation pulse and the refocusing pulses is $t_s/2$. The noise increases in proportion to the Square root of the number of echoes summed.

From equation 13, we can obtain an equation for the relative improvement R(M), which is the ratio between the S/N ratio with M echoes to the S/N ratio from the first echo alone.

$$R(M) = \frac{1}{\sqrt{M}} \int_{m=1}^{M} \text{Exp}(-(m-1)T_2^{**}/T_2)dm \quad (14)$$

Figure 9:
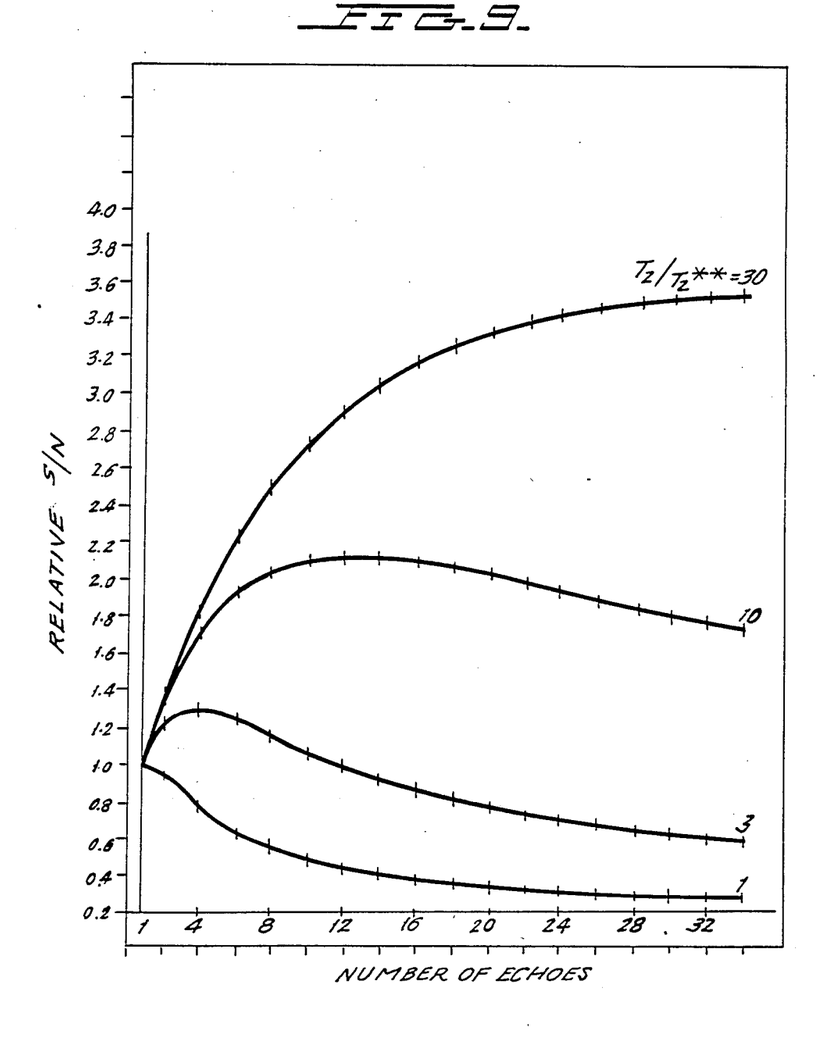
FIG. 9 is a graph showing the improvement of the relative signal-to-noise ratio as the number of echoes sampled increases.

Equation 14 is plotted in FIG. 9 for several values of $T_2/T_2^{}$, illustrating the relative S/N ratio resulting from the addition of various numbers of echoes for each value of $T_2/T_2^{}$. If $T_2/T_2^{} > 1$, some gain in sensitivity is possible by adding echoes. The operator may vary the value of $T_2/T_2^{}$ to some extent by the choice of resolution and by setting the acceptable degree of spatial distortion. This ratio becomes particularly important at higher field strengths, since magnets for imaging applications are presently specified with the same order of inhomogeneity regardless of the maximum field strength. Therefore assuming the same relative inhomogeneity, the ratio of $T_2/T_2^{}$ is much larger at higher fields than at lower fields and the value of R(M) in equation 14 is increased. For example, from equation 14, if $T_2/T_2^{} = 3$, the fourth echo has an intensity of 37% of the first echo and a sensitivity improvement of 30% is achieved by sampling four echoes. On the other hand, if $T_2/T_2^{**} = 30$, a sensitivity improvement of 355% is achievable by sampling 38 echoes.

A number of straightforward variations of the present invention are apparent from the above disclosure. For example, further signal averaging could be obtained by adding the data sets resulting from more than one excitation pulse, provided that the phase encoding gradients are equal. Also, other pulse and gradient switching sequences closely resembling pulse and gradient switching sequence 30, disclosed above, could be used to obtain the necessary spin echoes to be coherently added.

Although the invention has been described in connection with a plurality of preferred embodiments, many other variations and modifications will now become apparent to those skilled in the art. It is preferred, therefore, that the present invention be limited not by the specific disclosure herein, but only by the appended claims.

I claim:

1. A method of generating an NMR image of an object, comprising:
    applying a sequence of stimulating signals to an object in such a manner as to produce a plurality of groups of echoing NMR signals with both real and imaginary components containing phase encoded information;
    adding the echoing NMR signals of each of said plurality of groups of echoing NMR signals to obtain a respective data set for each group, the adding step including preserving the phase encoded information from both the real and imaginary components of the echoing NMR signals;
    combining the respective data sets to obtain a combined data set including the phase encoded information from both the real and imaginary components of the echoing NMR signals of each respective data set; and
    performing a phase-dependent transform of the combined data set to obtain an NMR image of the object.

2. The method of claim 1, in which the combining step comprises cancelling any baseline offsets of the echoing NMR signals.

3. The method of claim 1 in which the applying step comprises the substeps of applying an excitation pulse and then applying a sequence of refocusing pulses.

4. The method of claim 3 in which the substep of applying the sequence of refocusing pulses comprises applying refocusing pulses having non-ideal characteristics and compensating for the non-ideal characteristics of the pulses.

5. The method of claim 4 in which compensating for the non-ideal characteristics of the pulses comprises repeating a subsequence of four refocusing pulses, each repetition of the subsequence comprising applying the four refocusing pulses alternately along first and second orthogonal axes.

6. The method of claim 3 in which the substep of applying the excitation pulse further comprises applying a gradient field to select a plane of the object to be imaged.

7. The method of claim 3 in which each of the refocusing pulses produces one of the echoing NMR signals, the adding step comprising adding the echoing NMR signals from the refocusing pulses following the excitation pulse to obtain a combined signal.

8. The method of claim 7 in which the adding step further comprises transforming the combined signal to obtain a respective data set.

9. The method of claim 8 in which the applying step further comprises applying a plurality of excitation pulses like the first-mentioned excitation pulse and including the first-mentioned excitation pulse, the applying step further comprising applying a respective sequence of refocusing pulses like the first-mentioned sequence of refocusing pulses after each excitation pulse; the adding step further comprising adding the echoing NMR signals from each respective sequence of refocusing pulses to obtain a respective combined signal like the first-mentioned combined signal and transforming each respective combined signal to obtain a respective data set like the first-mentioned respective data set.

10. The method of claim 8 in which the applying step further comprises applying a plurality of excitation pulses like the first-mentioned excitation pulse and including the first-mentioned excitation pulse, the applying step further comprising applying a respective sequence of refocusing pulses like the first-mentioned sequence of refocusing pulses after each excitation pulse; the adding step further comprising adding the echoing NMR signals from at least two of the sequences of refocusing pulses to obtain a respective combined signal like the first-mentioned combined signal, the respective combined signal being averaged; the adding step further comprising transforming each respective combined signal to obtain a respective data set like the first-mentioned respective data set.

11. The method of claim 7 in which the substep of adding the echoing NMR signals comprises obtaining a time reversed signal of each alternative one of the echoing NMR signals, obtaining a complex conjugate signal of each of the time reversed signals, and adding each complex conjugate signal to the preceding echoing NMR signal.

12. An apparatus for generating an NMR image of an object comprising:
  applying means for applying stimulating signals to an object, the applying means being operable for applying a sequence of stimulating signals to the object for producing a plurality of groups of echoing NMR signals from both real and imaginary components of the echoing NMR signals containing phase encoded information;
  adding means for adding the echoing NMR signals of each of said groups of echoing NMR signals in such a manner as to obtain a respective data set for each group, the adding means also being for preserving the phase encoded information from both the real and imaginary components of the echoing NMR signals;
  combining means for combining the respective data sets for obtaining a combined data set including the phase encoded information from both the real and imaginary components of the echoing NMR signals of each respective data set; and
  a transforming means for performing a phase-dependent transform on the combined data set for providing an NMR image of the object.

* * * * *